(12) United States Patent
Bär et al.

(10) Patent No.: US 8,393,735 B2
(45) Date of Patent: Mar. 12, 2013

(54) FUNDUS CAMERA OBJECTIVE AND CAMERA HAVING SUCH FUNDUS CAMERA OBJECTIVE

(75) Inventors: Leopold Bär, Sulz im Wienerwald (AT); Ingeborg Fromberg, Hennigsdorf (DE)

(73) Assignee: S & V Technologies AG, Hennigsdorf (DE)

( * ) Notice: Subject to any disclaimer, the term of this patent is extended or adjusted under 35 U.S.C. 154(b) by 123 days.

(21) Appl. No.: 12/864,421

(22) PCT Filed: Jan. 23, 2009

(86) PCT No.: PCT/EP2009/000429
§ 371 (c)(1),
(2), (4) Date: Sep. 20, 2010

(87) PCT Pub. No.: WO2009/092598
PCT Pub. Date: Jul. 30, 2009

(65) Prior Publication Data
US 2011/0013139 A1   Jan. 20, 2011

(30) Foreign Application Priority Data
Jan. 24, 2008 (AD) .................................. A 99/2008

(51) Int. Cl.
*A61B 3/14* (2006.01)
*A61B 3/10* (2006.01)

(52) U.S. Cl. ......... 351/206; 351/205; 351/213; 351/221

(58) Field of Classification Search ........... 351/200–246
See application file for complete search history.

(56) References Cited

U.S. PATENT DOCUMENTS

| 7,048,379 B2 * | 5/2006 | Miller et al. .................. 351/213 |
| 2005/0041207 A1 | 2/2005 | Miller et al. |
| 2005/0200707 A1 | 9/2005 | Yogesan et al. |

FOREIGN PATENT DOCUMENTS

| DE | 202006000562 U1 | 5/2006 |
| WO | WO2004/017825 A1 | 3/2004 |
| WO | WO2005/122874 A1 | 12/2005 |

* cited by examiner

*Primary Examiner* — Mohammed Hasan
(74) *Attorney, Agent, or Firm* — Muncy, Geissler, Olds & Lowe, PLLC

(57) ABSTRACT

The invention relates to a fundus camera objective for recording an eye fundus. The invention further relates to a camera (30) having a fundus camera objective (20). Moreover, the invention relates to a ring light (18) that is connected to the fundus camera objective (20) or a camera (30) and serves the purpose of illuminating the eye (4) surroundings. The fundus camera objective (20) can be connected to a general analog or digital camera (30), it being possible to replace individual components and thus to adapt easily to more modern cameras or other intended uses. The fundus camera objective for recording an eye fundus comprises an objective (22), a tube (19) and an ocular (28), the fundus camera objective (20) having a fundus camera objective connection unit (31) on the camera side and being capable of coupling to a camera (30) via the fundus camera objective connection unit (31).

19 Claims, 2 Drawing Sheets

FUNDUS CAMERA OBJECTIVE AND CAMERA HAVING SUCH FUNDUS CAMERA OBJECTIVE

BACKGROUND OF THE INVENTION

Field of the invention

The invention relates to a fundus camera objective for recording an eye fundus. The invention further relates to a camera having a fundus camera objective. Moreover, the invention relates to a ring light that is connected to the fundus camera objective or a camera and serves the purpose of illuminating the eye surroundings.

Description Of The Related Art

A fundus camera can be used to make a precise recording of the eye fundus in which, in particular, it is possible to display the retina, blood vessels, the optic nerve and the choroidal membrane. The fundus camera is used for the diagnosis of changes in the eye and for monitoring disease progressions. Conventional fundus cameras are offered by various manufacturers and are designed as special cameras with a special objective. Camera and objective are in this case arranged in a common housing and coupled to an image processing unit via a connecting cable.

A first disadvantage of the conventional fundus cameras is that the latter are connected to an image processing base station via cables and lines. Moreover, conventional fundus cameras have a high dead weight. A further disadvantage consists in that the components of the camera cannot be replaced by the final user, and therefore cannot be adapted to further developments or innovations and/or different applications. In the case of conventional fundus cameras, it is not possible to replace either the objective or components of the objective, nor is it possible to change the image resolution, storage capacity or image processing functionality of the taking camera. The conventional devices are mostly very expensive, since the piece numbers are low.

Conventional digital cameras have undergone a rapid development in recent years, particularly in the range of resolution and in the image processing functionality.

To date, no fundus camera objectives are known that are separately available and can be connected to various analog and/or digital cameras.

The object therefore arises of specifying a fundus camera objective and a camera, it being possible to connect the fundus camera objective to a general analog or digital camera, individual components being replaceable, and it thus being possible to make a simple adaptation to more modern cameras or other intended uses.

The object is achieved by a fundus camera objective for recording an eye fundus as claimed in claim 1.

SUMMARY OF THE INVENTION

The core of the invention is a fundus camera objective having a fundus camera objective connection unit that enables a connection to an analog or digital camera.

The fundus camera objective has the usual optical components such as objective, tube and ocular. The fundus camera objective connection unit is designed such that it can be connected to conventional analog or digital cameras. The user, in particular the ophthalmologist, is thereby enabled to acquire a fundus camera objective and to use the latter over a relatively long time period, it being possible for the camera used as fundus camera to be more frequently replaced, thus enabling an adaptation to the respective state of development of such cameras.

The tube of the fundus camera objective can be adjusted, and so the distance between the objective and ocular can be set in order thereby to enable an adaptation to different applications.

In order to illuminate the eye fundus that is to be recorded, and/or to illuminate the surroundings, a ring light is preferably provided that is arranged in the front area of the fundus camera objective and is coupled to an external light source that feeds light to the ring light. The ring light can be connected to a beam splitter into which light is coupled from an external light source and/or a flashlight. Alternatively, it is possible for the ring light to be connected to an illumination unit that can output both light of a predetermined wavelength, and a flashlight. There is no need for a beam splitter when use is made of such an illumination unit. The beam splitter preferably has two inputs and at least one output, an external light source being connected to one of the inputs, and a flashlight being connected to the other input. The flashlight of the camera can preferably be used as flashlight. The at least one output of the beam splitter can be coupled to the ring light. Present at the input of the beam splitter, which is connected to the flashlight, is a beam shaper that adapts the cross section of the flashlight of the camera or of a separate flash tube to the cross section of the beam splitter.

It is also provided to connect the fundus camera objective to a handle that enables the fundus camera objective to be operated with one hand. It is preferably possible for batteries or rechargeable batteries that provide a supply of energy, for example for the camera, for an external flashlight and/or for the external light source for the ring light to be provided in this handle. The handle preferably has a release that transmits a release signal to the camera via a mechanical wire release, an electric line or a radio, and triggers a recording there.

The fundus camera objective is preferably equipped with a reversing optics that turns a recorded image round in order thereby to obtain an erect image. The reversing optics is not necessarily required when a digital camera is connected, since later image processing can provide automatic image reversal in order to display an erect image.

The fundus camera objective preferably has a setting device for diopter compensation which is achieved by displacing the objective and ocular relative to one another. The compensated diopters can be read out on a scale on the outside of the tube.

The fundus camera objective can also have a field diaphragm that is inserted into the beam path of the fundus camera objective and is configured in the form of an iris diaphragm, for example. This field diaphragm can be used to change the diameter of the beam path. The diameter of the field diaphragm can be adjusted via a diaphragm setting ring arranged on the outer circumference of the fundus camera objective.

However, it is also possible as an alternative to an adjustable field diaphragm to use a field diaphragm having a fixed diaphragm width. The tube of the fundus camera objective can further have filters that, for example, undertake color filtering in order to adapt the fundus camera objective for various applications in the examination of the eye.

In an advantageous refinement, the fundus camera objective can be configured for recording such that it is possible to take an angiography photograph of the eye fundus. A contrast agent, for example fluorescein is injected by way of example into the arm or foreleg vein in order to display the blood vessels of the retina photographically. The fundus camera objective requires for an angiography photograph an excitation filter that filters the white light fed such that only blue light with a wavelength of approximately 480 nm strikes the retina. The fluorescein molecules are excited in this case and emit green light. However, blue light is also reflected and guided to the beam path of the fundus camera objective. Arranged there is a blocking filter that filters out the blue component of the light such that only a green light component with a wavelength of 510 to 530 nm can penetrate to the fundus camera, an angiography photograph of the retina thereby being enabled.

The ring light is preferably connected via a light guide to the beam splitter or to an external light source or to an illumination unit, it being possible to set the amount of light fed to the ring light. The camera connection unit is preferably configured as a thread, or has a bayonet lock such that the fundus camera objective can be connected to a conventional analog or digital camera with the aid of the fundus camera objective connection unit.

Moreover, the object is also achieved by a camera having a fundus camera objective as described above, the camera having a camera connection unit that enables a connection of the fundus camera objective and, in particular, of the fundus camera objective connection unit. The camera connection unit therefore preferably likewise has a corresponding thread or else is designed such that a fundus camera objective can be connected to the camera with the aid of a bayonet lock.

The camera used as fundus camera can be a conventional analog or digital camera and therefore has a display, a memory for example in the form of a memory card, and an image processor that enables image processing.

As an alternative to being fastened on the fundus camera objective, the above-described handle can also be fastened directly to the fundus camera, it also being possible in this case to supply energy both to the camera and to the ring light or the external light source and/or the flashlight via rechargeable batteries or batteries in the handle.

Irrespective of the location where it is fastened, the handle can preferably comprise a light source or illumination unit whose light either can be coupled into the beam splitter or can be fed directly to the ring light. It is thereby possible to integrate in the handle a light source which is supplied with energy directly via the batteries or rechargeable batteries in the handle and the luminous intensity of which can be set directly at the handle, the only thing thereby remaining necessary to do being to lead the light to the ring light via a light guide, for example.

A further aspect of the invention relates to the ring light, which enables a better illumination of macrophotographs, the ring light radiating its light in the direction of the eye and therefore illuminating the eye. The ring light can preferably be coupled via a light guide to an external light source, or else be connected to a flashlight. Alternatively, it is possible for the ring light to be coupled to the previously described beam splitter to which it is possible to connect an external light source and a flashlight. The ring light can also be used without a fundus camera objective and be connected to a normal analog or digital camera in order to enable better illumination during macrophotography.

BRIEF DESCRIPTION OF THE DRAWINGS

The invention is explained in more detail below with the aid of the figures, in which.

DETAILED DESCRIPTION OF THE INVENTION

Figure 1:
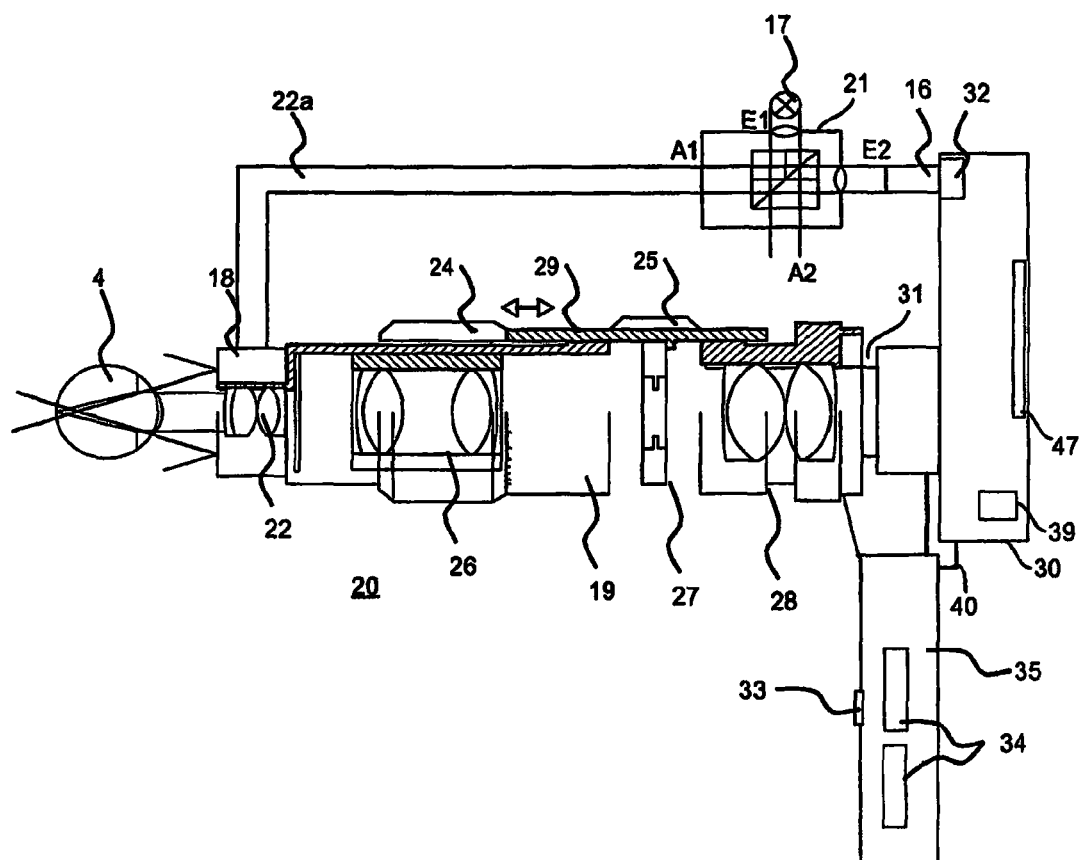
FIG. 1 shows a design of an inventive fundus camera objective that is connected to a fundus camera.

In accordance with FIG. 1, the inventive fundus camera objective 20 is connected to a digital or analog camera 30. To this end, the fundus camera objective 20 has a fundus camera objective connection unit 31 that can be coupled to a camera connection unit 36. The camera connection unit 36 is, for example, configured as an internal thread, the fundus camera objective connection 31 having an external thread. Alternatively, a bayonet lock is possible between the fundus camera objective connection 31 and camera connection unit 36.

The retina of the eye 4 is irradiated with light that is radiated by the ring light 18. The light beams coming from the retina of the eye 4 leave the eye and are carried to the fundus camera objective and strike an objective 22 there in a parallel fashion. The beam path runs inside the tube 19 of the fundus camera objective 20 and leaves the fundus camera objective via the ocular 28 arranged on the camera side so as to impinge on a film in an analog camera or a photosensitive sensor, for example a CCD sensor, in a digital camera. In this case, the focal length of the camera 20 is preferably set to "infinity". The image is stored on the image recording medium and held ready for further evaluation of the photograph. Given a digital camera, there is provided for this purpose a signal processor that can undertake image processing and transmits the image stored on the CCD sensor to a nonvolatile memory, for example in the form of a memory card. Given an analog camera, it is necessary to develop the film.

The fundus camera objective 20 preferably comprises a reversing optics 26 for the purpose of being able to produce an erect image of the eye, it being possible, however, to omit the reversing optics 26 given a digital camera, since the image can be rotated electronically in this case. Diopter compensation that can be implemented by a setting ring 24 is provided for the purpose of compensating any possible ametropia of the eye. To this end, there is arranged on the outer side of the tube 19 a scale 29 that enables the compensated diopters to be read off. The diopter compensation is required for the parallel alignment of the beams that leave the fundus camera objective. The lenses of the objective 22 and of the ocular 28 are displaced relative to one another inside the fundus camera objective 20 by rotating the setting ring 24.

The fundus camera objective 20 further has a field diaphragm 27 that is configured as an iris diaphragm, it being possible to adjust the diameter of the diaphragm by rotating a setting ring 25. Alternatively, the diaphragm 27 can also be configured as a fixed diaphragm. The tube 19 can have filters at various locations within the beam path. It is likewise possible to arrange a replaceable attached filter upstream of the objective 22 of the fundus camera objective.

Provided for illuminating the eye to be recorded is a fiber optic ring light 18 which is mounted in the front area of the fundus camera objective 20 and radiates light in the direction of the eye. In this case, the ring light 18 can have various diameters, for example, 2.5 cm, and can therefore be adapted to various applications and to various patients (children, adults). The ring light 18 is connected to a beam splitter 21 via a light guide cable 22a. An external light source 17 of dimmable configuration is preferably connected to the beam splitter 21. Again, a flashlight 32 is connected to the beam splitters via an input E2. The flashlight 32 on the camera 30 can be used in this case. However, it is also possible to use an external flashlight. The flashlight is preferably coupled into the beam splitter 21 via a beam shaper 16.

The beam splitter 21 serves for uniting the light from the external light source 17 and the flashlight 32. Light beams that enter at the two inputs E1 and E2 are combined in the beam splitter 21 and reemerge at the at least one output A1. The second output A2 is open in FIG. 1 and can be used to connect a second possibility of illumination, for example for illuminating the surroundings. Connected respectively to the output A1 and, if appropriate, also to the output A2 is a light cable 22a with the aid of which the light output by the beam splitter 21 is guided to the ring light 18 or to the further possibility of illumination. An external light source 17 is mounted at the input E1. If appropriate, an optics can be provided for focusing. It is likewise possible to use an insertable filter to filter the light as early as coupling in upstream of the beam splitter 21.

An IR light source 17 can also be connected also to be able to apply the fundus camera or the fundus camera objective 20 in the non-mydriatic fashion, that is to say without artificially dilating the pupil. In order for the entire amount of light from the external light source 17 or of the flashlight 32 to be coupled into the light guide cable 22a, an optical lens arranged respectively at the input E1 or E2 focuses the light such that the entire cross section of the light guide cable 22a is illuminated. The beam shaper 16 at the input E2 comprises light guide fibers which are shaped such that the cross section at the end facing the beam splitter 21 is round. The other end of the light guide fibers is designed such that it corresponds to the cross section of the camera flash 32 and is mostly of square design. The flash 32 can be built into the camera 30. However, it is also possible to use an external flash unit. The beam shaper 16 is mounted in this case upstream of the respective flashlight 32 such that the emission from the flashlight is further guided to the ring light 18 by the beam shaper 16 and the beam splitter 21 via the light guide cable 22a, the result being to enable the fundus of the eye 4 to be illuminated. The illumination beam of the external light source 17 and the light beam from the flashlight 32 are coupled in the beam splitter 21 into a common beam path, the emission of the flashlight passing over this path to the eye fundus in order to provide the latter with sufficient illumination for the time of the recording. In order to guide as much light as possible to the eye, the light guide cable 22a can be connected to both outputs A1 and A2, and thus the light can be fed to the ring light 18. Alternatively, it is possible for a further illumination source to be connected to the output A2 in order to implement a further illumination of the object to be recorded. When both outputs A1 and A2 are connected to the light guide cable 22a, the light yield is virtually 100%, since only 50% of the incident light is available at each output A1 and A2 of the beam splitter 21.

The fundus of the eye 4 is illuminated via the ring light 18. So that no interfering reflections occur on the cornea, the illumination beam path and the observation beam path are separated from one another.

The illumination takes place laterally past the observation beam path. The amount of light that is fed from the external light source 17 or from the illumination unit 38 can be regulated via a dimmer or potentiometer 41 (see FIG. 2).

So as to be able to operate the fundus camera 30 and the fundus camera objective 20 connected to the fundus camera in a simple fashion and also using only one hand, it is preferred to provide a handle 35 that is supported in the area of the camera connection unit 36 and/or of the fundus camera objective connection unit 31. In this case, the handle 35 can be fastened via a connection unit (not specified in more detail) on the outer circumference of the fundus camera objective. The handle 35 preferably has a release 33 that is connected to the camera via a connection 40 and enables recording to be triggered. It is also possible to arrange in the handle 35 batteries and/or rechargeable batteries 34 that make a power supply available, for example to the camera 30, external illumination source 17, 38 and/or the flashlight 32. The triggering of the recording can alternatively also be performed via a mechanical rod assembly or a wire release. The release command can also be transmitted to the camera 30 by radio. It is also possible to install in the handle 35 a potentiometer 41a that can be used to set the illuminance of a ring light 18. Moreover, additional operating elements for focusing and/or for image processing can be arranged in the handle 35. The handle 35 can also be used without the fundus camera objective 20 when, for example, a heavy telescopic objective is connected to the analog or digital camera 30. Through the use of the handle 35, the camera together with the heavy telescopic objective can be manipulated more easily such that it is even possible to hold the camera with one hand.

Figure 3:
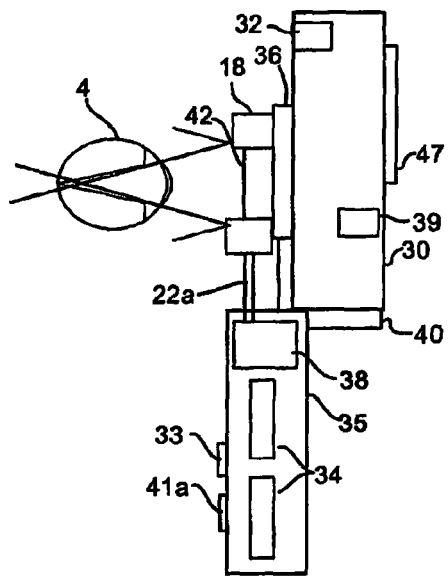
FIG. 3 shows a camera that is coupled to an inventive ring light and is supported by an inventive handle.

The ring light 18 can also be used without the fundus camera objective 20. This is illustrated in FIG. 3. In accordance with FIG. 3, the ring light 18 is directly attached to the camera connection unit 36 in order to improve the illumination, for example when recording the eye. The camera 30 is connected to a general objective 42 on the camera connection unit 36. In the case of macrophotographs with the aid of digital cameras, the integrated camera flash 32 mostly cannot be used, since the illumination during the macrophotograph is insufficient and, owing to the lateral offset of the flashlight 32 in relation to the objective 42, the object to be photographed can no longer be adequately illuminated. In order to enable adequate illumination, even without a fundus camera objective the ring light 18 can thus enable an illumination closely around the object to be photographed. With an appropriate attachment on the fundus camera objective 20 or even on the general objective 42, the camera can also be used to photograph cavities such as ears, noses or throats, the attachment then being configured in dependence on application. An appropriately configured attachment can likewise be used to record images of the skin and changes thereof. Here, as well, the ring light ensures adequate illumination in the macrorange.

In FIG. 3, the handle 35 is supported on the camera connection unit 36 or on the objective 42. The handle 35 here includes an illumination unit 38 that guides light to the ring light 18 via a light guide cable 22a. The handle 35 is connected to the camera 30 via the connecting cable 40 in order to transmit commands of the operating elements 33, 41a etc. in the handle 35 to the camera 30. Alternatively, it is possible for the handle 35 to be supported solely on the camera 30.

Figure 2:
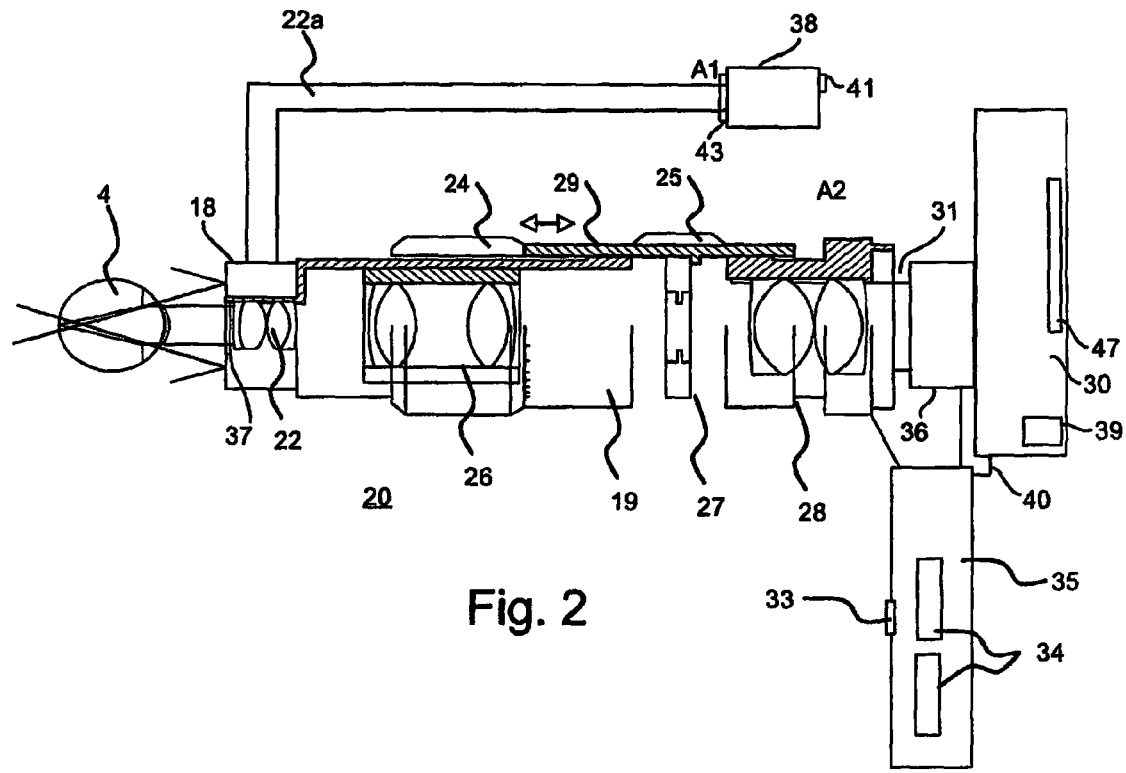
FIG. 2 shows an alternative refinement of an inventive fundus camera objective that is connected to a fundus camera.

Illustrated in FIG. 2 is an alternate embodiment that is based on the embodiment in accordance with FIG. 1. Here, the fundus camera objective 20 is configured together with an illumination unit 38 and the ring light 18 such that an angiography photograph of the blood vessels of the retina of the eye 4 can be obtained. On the one hand, this requires that light radiated by the illumination unit 38 be filtered via an excitation filter 43 such that only blue light, for example with a wavelength of 480 nm, enters the light guide 22a and is emitted via the ring light 18. A contrast agent, for example fluorescein, is injected into the arm vein of the patient before the angiography photograph, the blue light emitted by the illumination unit 38 and filtered by the excitation filter 43 being guided to the ring light 18 via the light guide 22a such that the blue light enters the eye. The blue light excites the fluorescein molecules such that a green light is emitted. However, blue light is also reflected in the direction of the fundus camera objective 20. The blue and green light then strikes a blocking filter 37 that is arranged as an attached filter upstream of the objective 22. The blocking filter 37 filters the reflected blue light out such that only the green light can penetrate into the fundus camera objective 20 and can thus be recorded by the camera 30. The green light in this case has a wavelength of approximately 510 to 530 nm.

Alternatively, the blocking filter 37 can also be arranged inside the fundus camera objective 20. However, implementation as an attached filter has the advantage that the fundus camera objective 20 can therefore also be adapted to other types of photographs and to other applications.

The illuminance of the illumination unit 38 can be set via a dimmer or potentiometer 41. Furthermore, depending on application the illumination unit 38 is provided with an internal light source and/or a flash tube, and therefore requires no beam splitter.

A beam splitter 21 as in the exemplary embodiment in accordance with FIG. 1 is not required when the illumination unit 38 is used with a light source that alongside its ability to be dimmed can also flash. The necessary flashlight for illuminating the eye fundus during the recording is then taken over by the light source in the illumination unit 38 instead of the camera flash.

It is likewise possible for this illumination unit 38 to be integrated directly in the handle 35, and thus for the required light to be fed to the eye via this ring light 18 in order to ensure high quality photographs. The illumination unit 38 can also be provided with light sources that emit light of various wavelengths. When the illumination unit 38 is capable of emitting blue light, there is, for example, no need to use the excitation filter 43, since the blue light is coupled into the ring light 18 directly via the light guide 22a, in order thus to emit blue light to excite the fluorescein molecules.

The retrofitting of a fundus camera with the fundus camera objective 20 in accordance with FIG. 2 is also possible for the refinement in accordance with FIG. 1.

Consequently, the inventive fundus camera objective can be used to replace individual components, with the result that the camera can be retrofitted straight away for various applications. Moreover, it is possible to connect the fundus camera objective 20 to various cameras in order thereby to employ the progress in development in the case of analog or digital cameras—including in use for eye examinations—without the frequent need to buy expensive and complex special fundus cameras in which the individual components cannot be replaced.

A conventional analog and digital camera can be upgraded to a fundus camera with the aid of the inventive fundus camera objective. This produces a compact design and, moreover, a low weight, the result being to enable operation with one hand. Moreover, there is no need to connect the camera together with the fundus camera objective to a base station via a cable or lines for the purpose of image processing.

The inventive handheld fundus camera can therefore be used, for example, in the veterinary sector, thereby facilitating recording in stalls or on the range where there is no possibility of an additional base station or cabling. Operating with one hand is possible owing to the handle together with release. Furthermore, additional operating elements such as release or dimmer on the handle 35 enable easier manipulation.

The invention claimed is:

1. A fundus camera objective for recording an eye fundus, comprising:
   an objective,
   an ocular,
   a tube, the optical length of the tube being adjustable in order to set a distance between the objective and ocular, wherein the fundus camera objective having a fundus camera objective connection unit on the camera side, and being connectable via the fundus camera objective connection unit to a camera,
   wherein the fundus camera objective is connected in the front area to a ring light, and
   wherein the ring light is coupled via a light guide to at least one of an external light source and a beam splitter, for feeding light of a predetermined wavelength to the ring light.

2. The fundus camera objective as claimed in claim 1, wherein the beam splitter has two inputs and at least one output, the at least one output being connectable to the ring light, wherein light from at least one of an external a light source and a flashlight are feedable to the inputs.

3. The fundus camera objective as claimed in claim 2, wherein the beam splitter is connected to a beam shaper that has at one of its ends the cross section of a flashlight of the camera or of a separate flash tube, and at the opposite end a round cross section with an optics for focusing on a cross section of the beam splitter.

4. The fundus camera objective as claimed in claim 1, wherein the fundus camera objective can be coupled to a handle, the handle comprises batteries or rechargeable batteries for supplying energy to one of the camera, the flashlight and the light source for the ring light.

5. The fundus camera objective as claimed in claim 1, wherein a removable handle has a release that can be coupled to the camera in order to trigger a recording.

6. The fundus camera objective as claimed claim 1, further comprising a reversing optics for providing an erect image.

7. The fundus camera objective as claimed in claim 1, wherein a setting device is provided for diopter compensation by displacing the objective and ocular relative to one another, it being possible to read out the compensated diopters on a scale on the outer tube.

8. The fundus camera objective as claimed in claim 1, wherein a field diaphragm is arranged in the beam path of the fundus camera objective, the diameter of the field diaphragm being adjustable via a diaphragm setting ring or a field diaphragm having a fixed diaphragm is arranged in the beam path of the fundus camera objective.

9. The fundus camera objective as claimed in claim 8, wherein the field diaphragm is an iris diaphragm.

10. The fundus camera objective as claimed in claim 1, wherein filters are present in the tube.

11. The fundus camera objective as claimed in claim 1, wherein an insertable excitation filter is arranged upstream of the ring light in order to allow passage of light of a predetermined wavelength, in particular blue light with a wavelength of approximately 480 nm, it being possible to insert in the beam path of the fundus camera objective a blocking filter that particularly allows passage of green light with a wavelength of approximately 510-530 nm.

12. The fundus camera objective as claimed in claim 1, wherein the amount of light fed to the ring light can be set.

13. The fundus camera objective as claimed in claim 1, wherein the fundus camera objective connection unit has a thread or a bayonet lock.

14. A camera having a fundus camera objective for recording an eye fundus, comprising:
   an objective,
   an ocular, a tube, the optical length of the tube can be adjusted in order to set the distance between the objective and ocular, wherein the fundus camera objective having a fundus camera objective connection unit on the camera side, and being connectable via the fundus camera objective connection unit to a camera, wherein the fundus camera objective is connected in the front area to a ring light, and wherein the ring light is coupled via a light guide to at least one of an external light source and a beam splitter, for feeding light of a predetermined wavelength to the ring light, the camera having a camera connection unit corresponding to the fundus camera objective connection unit.

15. The camera as claimed in claim 14 having at least one of a display unit, a processor for image conditioning and a memory for storing the photographs.

16. The camera as claimed in claim 14, wherein a handle is detachably fastened on the fundus camera, the handle having at least one of a release and batteries or rechargeable batteries, the batteries or rechargeable batteries supplying energy to at least one of the camera, the flashlight and the light source for the ring light, wherein the handle has a release that can be coupled to the camera in order to trigger a recording.

17. The camera as claimed in claim 16, wherein the handle comprises a light source, whose light can be coupled into the beam splitter or can be fed directly to the ring light.

18. The camera as claimed in claim 14, in which a beam shaper connected to the fundus camera objective can be connected to the flashlight of the camera.

19. A handle that can be connected to a camera as claimed in claim 14, the handle having at least one of a release and batteries or rechargeable batteries, the batteries or rechargeable batteries supplying energy to at least one of the camera, the flashlight and the light source for the ring light, and the release being connectable to the camera in order to trigger a recording.

* * * * *